United States Patent
Wang et al.

(10) Patent No.: US 11,576,918 B2
(45) Date of Patent: Feb. 14, 2023

(54) PHARMACEUTICAL COMPOSITION AND EXTRACT OF DENDROBII CAULIS WITH EYE CARE EFFECT AND USES OF PREPARING THE SAME THEREOF

(71) Applicant: AMX Pharma Inc., Taipei (TW)

(72) Inventors: Yi-Yueh Wang, Taipei (TW); Yun-Lian Lin, Taipei (TW); Wei-Hsiang Hsu, Taipei (TW)

(73) Assignee: AMX PHARMA INC., Taipei (TW)

( * ) Notice: Subject to any disclaimer, the term of this patent is extended or adjusted under 35 U.S.C. 154(b) by 266 days.

(21) Appl. No.: 16/796,893

(22) Filed: Feb. 20, 2020

(65) Prior Publication Data

US 2020/0261468 A1 Aug. 20, 2020

(30) Foreign Application Priority Data

Feb. 20, 2019 (TW) ................. 108105682

(51) Int. Cl.
*A61K 31/55* (2006.01)
*A61P 27/02* (2006.01)
*A61K 36/8984* (2006.01)

(52) U.S. Cl.
CPC .......... *A61K 31/55* (2013.01); *A61K 36/8984* (2013.01); *A61P 27/02* (2018.01)

(58) Field of Classification Search
None
See application file for complete search history.

(56) References Cited

U.S. PATENT DOCUMENTS 9,186,363 B1 11/2015 Parsonson
2019/0365668 A1* 12/2019 Chao ................ A61K 31/09

FOREIGN PATENT DOCUMENTS

| CN | 103520515 | 1/2014 |
| CN | 105669611 | 6/2016 |
| CN | 106581446 | 4/2017 |
| CN | 108635368 | 10/2018 |
| JP | 2008540348 | 11/2008 |
| KR | WO2018008803 | 1/2018 |
| TW | I294285 | 3/2006 |
| TW | I370126 | 4/2011 |
| TW | 201628635 | 8/2016 |

OTHER PUBLICATIONS

Wang, M.C., et al., Picrotoxane sesquiterpenoids from the stems of Dendrobium nobile and their absolute configurations and angiogenesis effect, Fitoterapia 121: 206-211 (2017)), abstract available at https://eurekamag.com/research/060/096/060096122.php, accessed on Jan. 10, 2022.*

Meng (Meng, C.W., et al., Picrotoxane sesquiterpenoids from the stems of Dendrobium nobile and their absolute configurations and angiogenesis effect, Fitoterapia 121 (2017) 206-211).*

Xu, J et al., Chemistry, bioactivity and quality control of Dendrobium, a commonly used tonic herb in traditional Chinese medicine, Phytochem Rev (2013) 12:341-367.*

Chunsheng Zhao, Qunfang Liu, Fathi Halaweish, Baoping Shao, Yuqing Ye and Weimin Zhao, Copacamphane, Picrotoxane, and Alloaromadendrane Sesquiterpene Glycosides and Phenolic Glycosides from Dendrobium moniliforme, Journal of Natural Products, 2003, vol. 66, No. 8, pp. 1140-1143.

Xue Zhang, Feng-Juan Tu, Hai-Yang Yu, Nai-Li Wang, Zhao Wang and Xin-Sheng Yao, Copacamphane, Picrotoxane and Cyclocopacamphane Sesquiterpenes from Dendrobium nobile, Chemical and Pharmaceutical Bulletin (2008) vol. 56, No. 6, pp. 854-857.

Wen-Haur Chao, Ming-Yi Lai, Hwai-Tzong Pan, Huei-Wen Shiu, Mi-Mi Chen and Hsiao-Ming Chao, Dendrobium nobile Lindley and its bibenzyl component moscatilin are able to protect retinal cells from ischemia/hypoxia by dowregulating placental growth factor and upregulating Norrie disease protein, BMC Complementary and Alternative Medicine (2018) 18:193, 16 pages.

Yau Lam, Tzi Bun Ng, Ren Ming Yao, Jun Shi, Kai Xu, Stephen Cho Wing Sze and Kalin Yanbo Zhang, Evaluation of Chemical Constituents and Important Mechanism of Pharmacological Biology in Dendrobium Plants, Evidence-Based Complementary and Alternative Medicine, vol. 2015, Article ID 841752, 25 pages.

Qinghua Ye, Guowei Qin and Weimin Zhao, Immunomodulatory sesquiterpene glycosides form Dendrobium nobile, Phytochemistry 61 (2002), pp. 885-890.

Xue Zhang, Hong-Wei Liu, Hao Gao, Hui-Ying Han, Nai-Li Wang Hou-Ming Wu, Xin-Sheng Yao and Zhao Wang, Nine New Sesquiterpenes from Dendrobium nobile, Helvetica Chimica Acta vol. 90 (2007), pp. 2386-2394.

Iao Yong Weix, Yan Long, Yu Jian Zhan, I-Chan Lix, Qin Xu and Chuan-Lei Xu, Study on the Prevention of Cataract in Rat Lens from Dendrobium nobile, Research and Practice of Chinese Medicines (2008) vol. 22, No. 2, pp. 27-31.

Yan Long, The Preliminary Study of Screening the Active Substance from Dendrobium. with the Function of Preventing Sugar Cataract and Screening Its Target Proteins, Chinese Master's Theses Full-text Database Medicine and Health Sciences, published on Aug. 16, 2008.

Nguyen Thi Viet Thanha,, Giang Thi Phuong Lya, Le Huyen Trama, Bui Huu Taib, Vu Quoc Huyc and Phan Van Kiemb, A New Picrotoxane Sesquiterpene Glucoside from Dendrobium nobile. Natural Product Communications vol. 12 (12) 2017.

Ying Shu, Dong-Ming Zhang and Shun-Xing Guo, A New Sesquiterpene Glycoside From Dendrobium Nobile Lindl, Journal of Asian Natural Products Research, Dec. 2004, vol. 6(4). pp. 311-314.

(Continued)

*Primary Examiner* — H. Sarah Park
(74) *Attorney, Agent, or Firm* — Raymond Chan

(57) ABSTRACT

The present invention provides an extract of Dendrobii Caulis with eye care effect, wherein the extract of Dendrobii Caulis has an active ingredient comprising a picrotoxane-type sesquiterpene. The present invention further provides a pharmaceutical composition with eye care and a use of an extract of Dendrobii Caulis for preparing a pharmaceutical composition with eye care effect.

3 Claims, 6 Drawing Sheets

(56) References Cited

OTHER PUBLICATIONS

Jia ju Zhou, Guirong Xie and Xinjian Yan, Encyclopedia of Traditional Chinese Medicines, Molecular Strcutures, Pharmacological Activities Natural Sources and Applications vol. 2: Isolated Compounds D-G.

Chun-Wang Meng, Yu-Lin He, Cheng Peng, Xing-Jie Ding, Li Guo and Liang Xiong, Picrotoxane sesquiterpenoids from the Stems of Dendrobium nobile and their absolute configurations and angiogenesis effect, Fitoterapia 121 (2017) 206-211.

Zhang Xue, Gso Hao, Han Hui-Ying, Liu Hong-Wei, Wang Nai-Li, Yao Xin-Sheng and Wang Zhao, Sesquiterpenes from Dendrobium Nobile, Chinese Traditional and Herbal Drugs, Dec. 2007, vol. 38 (12).

Weimin Zhao, Qinghua Ye, Xiaojian Tan, Hualiang Jiang, Xiaoyu Li, Kaixian Chen and A. Douglas Kinghom, Three New Sesquiterpene Glycosides from Dendrobium nobile with Immunomodulatory Activity, J. Nat. Prod. 2001, 64, 1196-1200.

Wen-Yi Chang and Agnes L.F. Chan, Dendrobium is used by some Chinese medicine pharmacy of medical center in current situation, The Journal of Taiwan Pharmacy, Jun. 30, 2010, vol. 26, No. 2.

\* cited by examiner

PHARMACEUTICAL COMPOSITION AND EXTRACT OF DENDROBII CAULIS WITH EYE CARE EFFECT AND USES OF PREPARING THE SAME THEREOF

NOTICE OF COPYRIGHT

A portion of the disclosure of this patent document contains material which is subject to copyright protection. The copyright owner has no objection to any reproduction by anyone of the patent disclosure, as it appears in the United States Patent and Trademark Office patent files or records, but otherwise reserves all copyright rights whatsoever.

BACKGROUND OF THE PRESENT INVENTION

Field of Invention

The present invention is related to a pharmaceutical composition and an extract of Dendrobii Caulis with eye care effect and a use of extract of Dendrobii Caulis for preparing the pharmaceutical composition, and more particularly, to a pharmaceutical composition having an active ingredient containing a picrotoxane-type sesquiterpene and an extract of Dendrobii Caulis with eye care effect and a use of extract of Dendrobii Caulis for preparing the pharmaceutical composition.

Description of Related Arts

According to Taiwan Herbal Pharmacopeia, Dendrobii Caulis is the fresh or dried stem of *Dendrobium nobile* Lindl., *Dendrobium loddigesii* Rolfe., *Dendrobium. chrysanthum* Wall. ex Lindl., *Dendrobium fimbriatum* Hook., *Dendrobium officinale* Kimura et Migo, *Dendrobium chrysotoxtum* Lindl. or *Dendrobium tosaense* Makino. Previous studies on Dendrobii Caulis have reported that various active compounds have been isolated, of which dendrobine is considered to be the main active ingredient; phenanthrenes have biological activities including anti-oxidation, anti-inflammatory, anti-tumor, etc.; sesquiterpenoids have immunomodulatory effects; polysaccharides have liver-protecting, immune regulation, anti-tumor and blood pressure lowering effects; bibenzyl compounds have anti-oxidation and anti-tumor effects. Although Dendrobii Caulis has been shown to have the effect of clearing the liver fire and improving eyesight, and a recent study has shown that in the application of eye diseases, moscatilin, one bibenzyl compound, in Dendrobii Caulis can protect retinal damage in the absence of oxygen. However, moscatilin is a less polar compound and it has been reported in the literature to have cytotoxicity and anti-tumor effect. Some studies also found that it is toxic to optic nerve cell strains and is not suitable as a medical drug for treating eye diseases. Clinically, there are no effective drugs with fewer side effects for treating cataracts, glaucoma, dry eye syndrome, etc. In addition, there is still not enough study indicating how Dendrobii Caulis exerts its eye-protecting effect on traditional Chinese medicine, and it is also unclear what the active ingredients is.

SUMMARY OF THE PRESENT INVENTION

The present invention therefore provides a pharmaceutical composition with eye care effect, an extract of Dendrobii Caulis and a use of the extract of Dendrobii Caulis for preparing a pharmaceutical composition, in which one salient feature thereof is to use a picrotoxane-type sesquiterpene as its active ingredients.

According to one embodiment, the present invention provides an extract of Dendrobii Caulis with eye care effect, wherein the extract of Dendrobii Caulis has an active ingredient comprising a picrotoxane-type sesquiterpene.

According to another embodiment, the present invention further provides a use of an extract of Dendrobii Caulis for preparing a pharmaceutical composition with eye care effect, wherein the extract of Dendrobii Caulis has an active ingredient comprising a picrotoxane-type sesquiterpene.

According to another embodiment, the present invention further provides a pharmaceutical composition with eye care, comprising a pharmaceutically acceptable carrier and an active ingredient, wherein the active ingredient comprises a picrotoxane-type sesquiterpene.

In the present invention, the extract of Dendrobii Caulis exhibits eye care effect, and the present invention further provides the principal active ingredients of the extract, showing its value on pharmaceutical use.

These and other objectives of the present invention will no doubt become obvious to those of ordinary skill in the art after reading the following detailed description of the preferred embodiment that is illustrated in the various figures and drawings.

DETAILED DESCRIPTION OF THE PREFERRED EMBODIMENT

Figure 1:
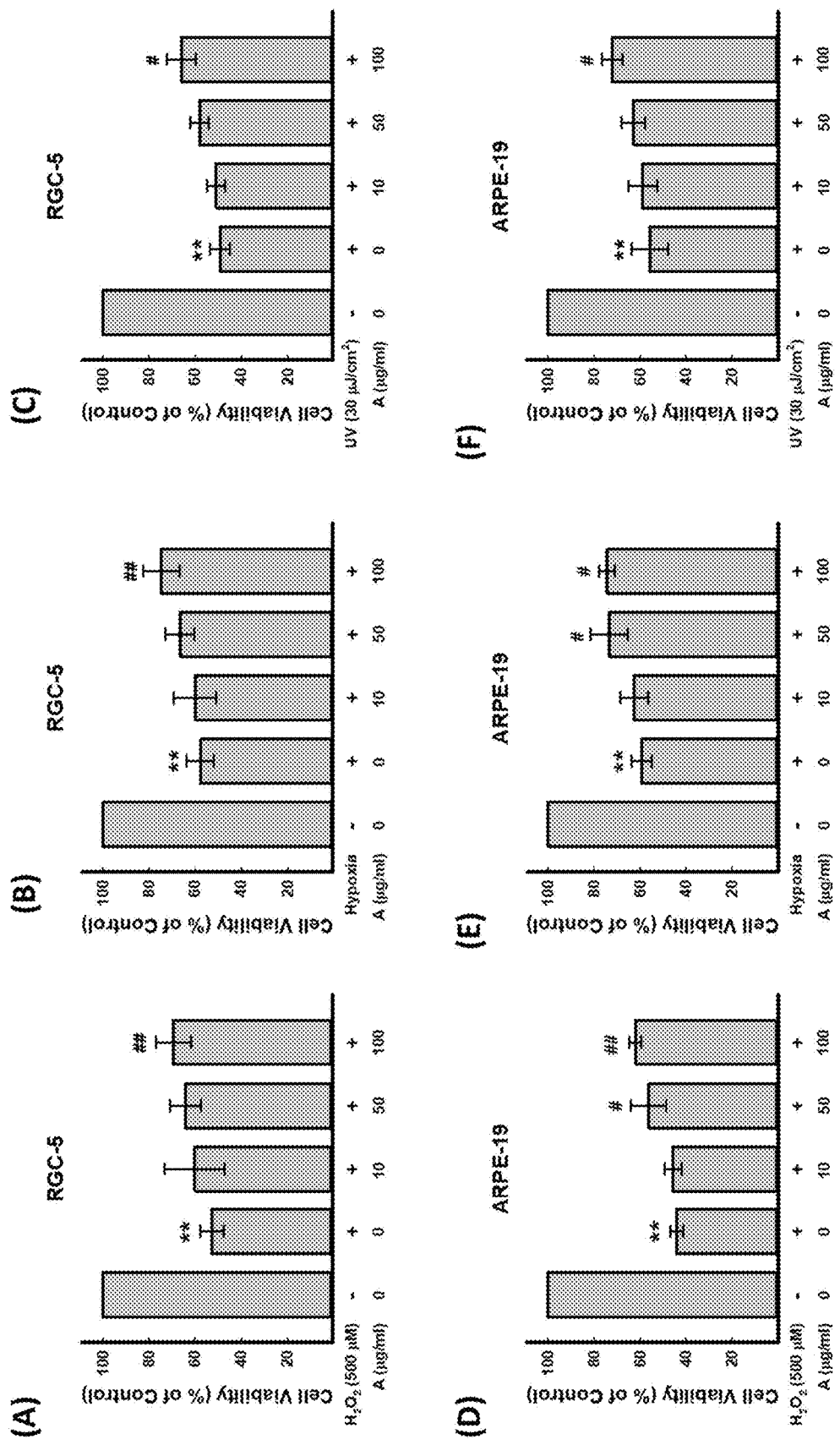
FIG. 1 shows the protection effect on RGC-5 and ARPE-19 cells with the administration of crude extract A against the damage induced by hydrogen peroxide, hypoxia and ultraviolet irradiation.

To provide a better understanding of the presented invention, preferred embodiments will be described in detail. The preferred embodiments of the present invention are illustrated in the accompanying drawings with numbered elements.

The present invention is directed to an extract of Dendrobii Caulis, and the preparation method thereof is shown below. First, commercially available the Dendrobii Caulis was extracted by 60-80% aqueous ethanol to obtain the crude extract A. In one embodiment, the Dendrobii Caulis refers to the dried stem of *D. nobile*, which is categorized into *Dendrobium* species, but it is not limited thereto. In other embodiments, it may be *D. officinale, D. chrysanthum, D. fimbriatum, D. chrysotoxum, D. tosaense* or *D. loddigesii*.

In one embodiment, the crude drug material refers to the stem of the *Dendrobium*. In one embodiment, crude extract A has a weight percentage of 10-16%.

Next, a macroporous resin chromatography is carried out and the column is eluted with water to obtain an aqueous sub-fraction A-1, and then is eluted with 40-60% ethanol/water to obtain another sub-fraction A-2. In one embodiment, the macroporous resin may be Diaion HP series resin developed by Mitsubishi Chemical Holdings Co. In one embodiment, the sub-fraction A-2 has a weight percentage of 3-6% with respect of the crude herb.

Next, the sub-fraction A-2 is purified first with Sephadex LH-20 column with methanol elution to give an sesquiterpenes containing fraction. Such fraction is then analyzed and separated by a preparative reverse phase chromatography column RP-18 with using 30%-45% methanol/water as mobile phase. A series of sesquiterpene compounds as the active ingredients can be obtained after repeated purification, in which one of such active ingredients is a picrotoxane type sesquiterpene. In one embodiment, the sesquiterpene compound can be represented by the structure of formula I:

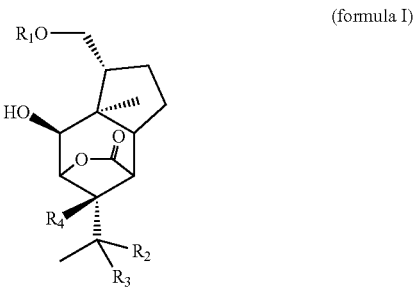

(formula I)

wherein $R_1$ may be H or a glucosyl group (Glc), $R_2$ may be H or OH, $R_3$ may be $CH_3$ or $CH_2OH$, and $R_4$ may be H or OH.

In one embodiment of the invention, the compound of formula I is dendromoniliside D (hereinafter "compound 1"), having the formula 2β, 3β, 11, 12-tetrahydroxypicrotoxan-3(15)-olide 11-O-β-D-glucopyranoside (IUPAC nomenclature: (1S, 4S, 5S, 5αR, 6R, 9S)-5-hydroxy-9-(2-hydroxypropan-2-yl)-5α-methyl-6-((((2R, 3R, 4S, 5S, 6R)-3,4,5-trihydroxy-6-(hydroxymethyl)tetrahydro-2H-pyran-2-yl)oxy)methyl)octahydro-2H-1,4-methanocyclopenta[d]oxepin-2-one), which can be represented by the following structural formula II:

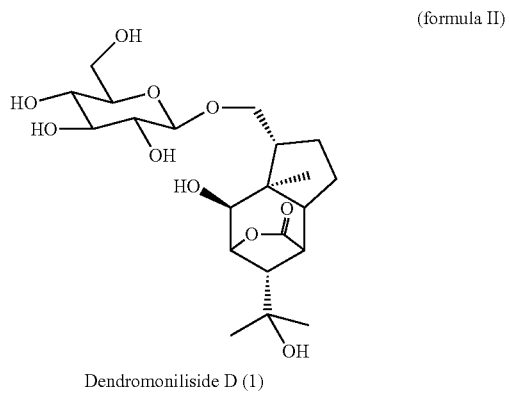

(formula II)

Dendromoniliside D (1)

In another embodiment of the present invention, the compound of formula I is dendrodensiflorol (hereinafter "compound 2"), having the formula 2β, 3β, 11, 12-tetrahydroxypicrotoxan-3 (15)-olide (IUPAC nomenclature: (1S, 4S, 5S, 5αR, 6R, 9S)-5-hydroxy-6-(hydroxymethyl)-9-(2-hydroxypropan-2-yl)-5α-methyloctahydro-2H-1,4-methanocyclopenta[d] oxepin-2-one), which can be represented by the following structural formula III:

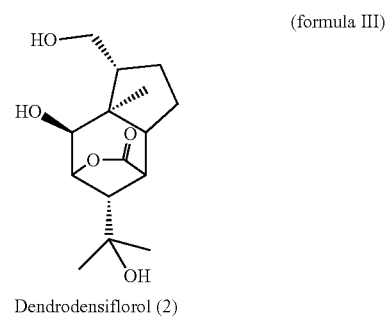

(formula III)

Dendrodensiflorol (2)

In another embodiment of the invention, the compound of formula I is dendronobil oliside A (hereinafter "compound 4"), having the chemical formula 2β, 3β, 11, 13-tetrahydroxypicrotoxan-3 (15)-olide 11-O-β-D-glucopyranoside (IUPAC nomenclature: (1S, 4S, 5S, 5αR, 6R, 9S)-5-hydroxyl-9-((S)-1-hydroxypropan-2-yl)-5-methyl-6-((((2R, 3R, 4S, 5S, 6R)-3,4,5-trihydroxy-6-(hydroxymethyl)-tetrahydro-2H-pyran-2-yl)-oxy) methyl) octahydro-2H-1,4-methanocyclopenta [d] oxepin-2-one), which may presented by the following structural formula IV:

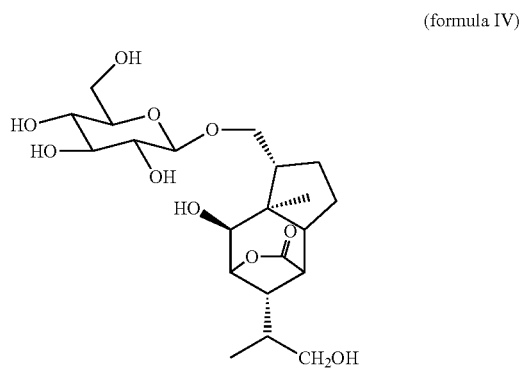

(formula IV)

Dendronobiloliside A (4)

In another embodiment of the present invention, the compound of formula I is dendroside G (hereinafter "compound 7"), having chemical formula 2β, 3β, 4, 11-Tetrahydroxypicrotoxan-3(15)-olide 11-O-β-D-glucopyranoside (IUPAC nomenclature: (1S,4R, 5S, 5αR, 6R, 9R)-5,9-dihydroxy-9-isopropyl-5α-methyl-6-((((2R, 3R, 4S, 5S, 6R)-3,4,5-trihydroxy-6-(hydroxy-methyl)tetrahydro-2H-pyran-2-yl)oxy)methyl)octahydro-2H-1,4-methanocyclopenta[d] oxepin-2-one), which can be represented by the following structural formula V:

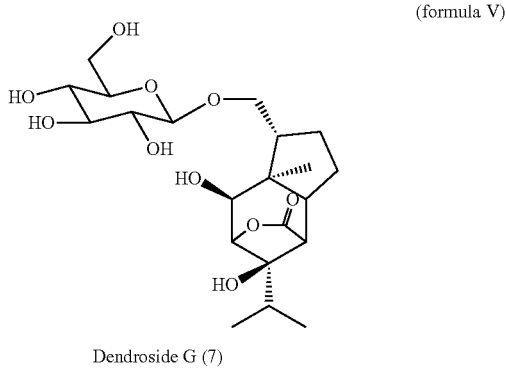

Dendroside G (7)

In one embodiment of the present invention, the active ingredient of formula I may comprise one of compound 1, compound 2, compound 4 or compound 7, two of which, three or even all of which. In one preferred embodiment, the active ingredient comprises compound 1 and compound 2, and the concentration of compound 1 is greater than that of compound 2. For example, the ratio of compound 1 to compound 2 in the extract is 3:1 to 10:1. In one embodiment, the active ingredient having the formula I has a weight percentage of 12-20% with respect to the sub-fraction A-2.

In one embodiment of the present invention, the sub-fraction A-2 further includes a dendrobine. In one embodiment, the dendrobine can be represented by following structural formula VI:

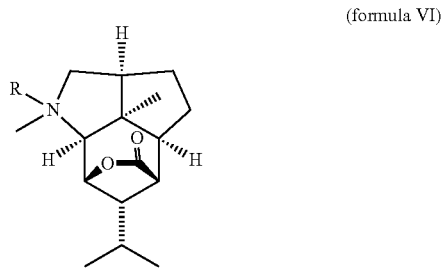

(formula VI)

In one embodiment, the dendrobine may be dendrobine (R=H) (hereinafter "compound 3"), N-methyldendrobinium (R=CH$_3$) (hereinafter "compound 5") or N-isopentenyl dendrobinium (R=isopentenyl) (hereinafter "compound 6"). In one embodiment, the weight percentage of the dendrobine is 20-35% with respect to the sub-fraction A-2.

Subsequently, the extract A, sub-fraction A-1, sub-fraction A-2 and the active ingredients (picrotoxane-type sesquiterpenes) are used to evaluate their biological activity on human retinal neuronal cells (ARPE-19) and optic nerve ganglion cells (RGC-5) after subjecting to hypoxia, hydrogen peroxide or ultraviolet radiation, in which the extract A, the sub-fraction A-2 and the active ingredient are shown to have eye care effect, and compound 1 (dendromoniliside D) and compound 2 (dendrodensiflorol) in the active fraction have significant eye care effect. The term "eye care effect" of the present invention refers the ability to give protection for optic nerve cells, the activation for neurons, or protection for optic nerve cells from cell senescence or cell death. More specifically, the active ingredient in the extract of Dendrobii Caulis can reduce the occurrence of eye diseases caused by radical, hypoxia or ultraviolet, such as cataracts, retinopathy and macular degeneration and glaucoma. The following context will describe the method of preparing the extracts with the active ingredient, and further describe the experiment to demonstrate the eye care effect of said extracts.

Experiment (A) Component Extraction and Analysis

Dendrobii Caulis were extracted with 60% ethanol/water at 50° C. for overnight. The extract was then concentrated under reduced pressure to obtain the crude extract A. The crude extract A was then introduced into a macroporous resin Diaion HP-20 and eluted with water to get an eluent which is then concentrated to obtain sub-fraction A-1. Thereafter, the column is eluted with 30-70% ethanol/water to obtain another eluent which is concentrated to obtain sub-fraction A-2. The sub-fraction A-2 was further purified by preparative reverse phase columns Sephadex LH-20 and RP-18 column to give pure compounds.

Figure 6:
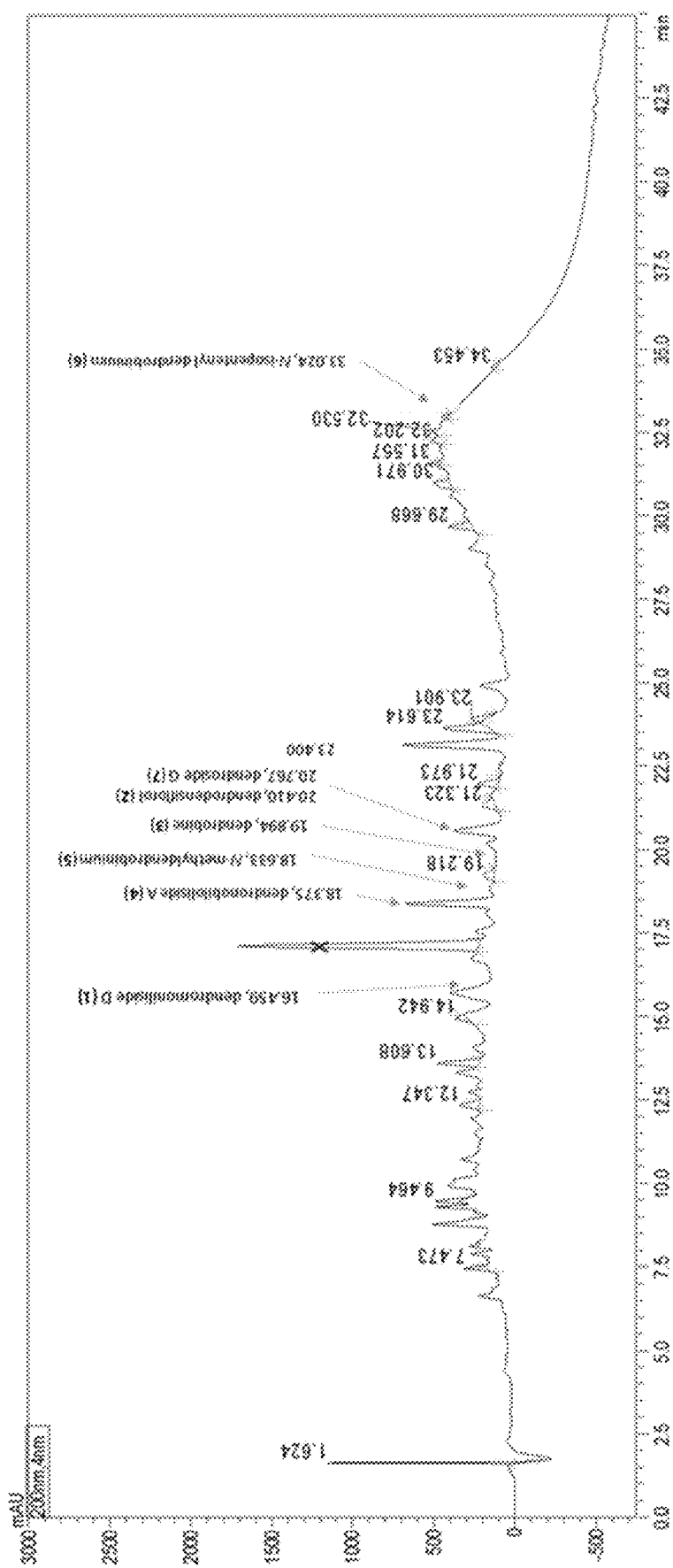
FIG. 6 shows the chemical profile of sub-fraction A-2 of Dendrobii Caulis by liquid chromatography tandem mass spectrometry (LC/MS).

The sub-fraction A-2 was further analyzed by liquid chromatography tandem mass spectrometry (LC/MS). Please refer to FIG. 6, which shows the chemical profile of the sub-fraction A-2 of Dendrobii Caulis. From FIG. 6, it is demonstrated that the extract contains sesquiterpenoid compound, 2β, 3β, 11, 12-tetrahydroxypicrotoxan-3(15)-olide 11-O-β-D-glucopyran-oside (compound 1; dendromoniliside D) (retention time: 16.459 minutes); 2β, 3β, 11, 12-tetrahydroxy-picrotoxan-3(15)-olide (compound 2; dendrodensiflorol)(retention time: 20.410 minutes); 2β, 3β, 11, 13-tetrahydroxypicrotoxan-3 (15)-olide 11-O-β-D-glucopyranoside (compound 4; dendronobiloliside A) (retention time: 18.375 minutes); 2β, 3β, 4, 11-tetrahydroxy picrotoxan picrotoxan-3(15)-olide 11-O-β-D-glucopyranoside (compound 7; Dendroside G) (retention time: 20.767 minutes), as well as alkaloid compounds including N-methyl-dendrobinium (compound 5) (retention time: 18.633 minutes), dendrobine (compound 3) (retention time: 19.894 minutes) and N-isopentenyl dendrobinium (compound 6) (retention time: 33.024 minutes) and other compounds. LC/MS analysis condition—instruments: Shimadzu LC-2040 C, LC/MS2020; analyzing column: Purospher® STAR, RP-18 endcapped (2 μm); mobile phase, solvent A: acetonitrile; solvent B: 0.1% formic acid; program: 0-2, 1-5% A; 2-8 min, 5-10% A; 8-18 min, 10-15% A; 18-20 min, 15% A; 20-25 mins, 15-20% A; 25-30 min, 20-30% A; 30-35 min, 30% A; 35-40 min, 30-70% A; 40-45 min, 70% A; injection volume 1 μl; flow rate: 0.2 ml/min.

(B) Optic Nerve Cell Activity Test

1. Cell Line and the Culture

The present experiment took human retinal cell (ARPE-19) and rat retinal ganglion cells (RGC-5) as model cell lines. ARPE-19 cells were cultured in DMEM-F12 medium containing 10% fetal bovine serum (FBS), 0.2% sodium bicarbonate and antibiotics (penicillin 100 units/ml, streptomycin 100 μg/ml); RGC-5 were cultured in DMEM medium containing 10% fetal bovine serum (FBS) and antibiotics (penicillin 100 units/ml, streptomycin 100 μg/ml).

2. Hydrogen Peroxide, Hypoxia and Ultraviolet Light-Induced Cell Injury

ARPE-19 and RGC-5 cells were seeded in 96-well plate. After 1 day, the cells were pre-treated with different concentrations of Dendrobii Caulis extract (A or A-2) or compounds 1-4 for 24 hours, and then exposed to (1) hydrogen peroxide (H$_2$O$_2$; 500 μM)) or (2) hypoxic environment or (3) ultraviolet (UV) irradiation (30 μJ/cm$^2$; three consecutive shots, for 60 seconds each with 60 second intervals, to trigger cell death. After 24-h culture, medium was removed and replaced with 10% precooled trichloroacetic acid (TCA)

to fix cells at 4° C. for 1 h, then washed with ddH$_2$O and dried. Next, 0.4% SRB 100 μl (w/v, in 1% acetic acid) was added to each well to stain the cells for 60 minutes, then washed several times with 1% acetic acid and dried plate.— The SRB in cells was dissolved in 150 μl of 10 mM Tris-HCl and measured the absorbance at 540 nm in an ELISA reader. The survival rate was calculated by comparing each treatment with the untreated control group as the 100% survival rate.

3. UVC-Induced Zebrafish Cataract Test

Zebrafish were randomly grouped (12 for each group) into blank control group, UVC irradiation group (300 μJ/cm$^2$) and UVC irradiation+treating group with A-2 at 0.495, 0.99, and 4.95 mg/ml three dosages or with compound 1 at 0.1 and 1.0 mM two dosages. The zebrafish were pre-fed with A-2 or compound 1 for one week, then subjected to UVC irradiation to observe the crystal change of the zebrafish daily. Before irradiating with UVC, the zebrafish is under anesthesia to expose only its eye to UVC (300 μJ/cm$^2$) for about 3 minutes, consecutively holding for seven days. The zebrafish eyes were observed every day. The severity of zebrafish cataract was scored from 1 to 3, depending on the clear level of the crystal body, in which the higher score represents the more turbidity of the crystal body. The scores are then plotted.

Results

Figure 2:
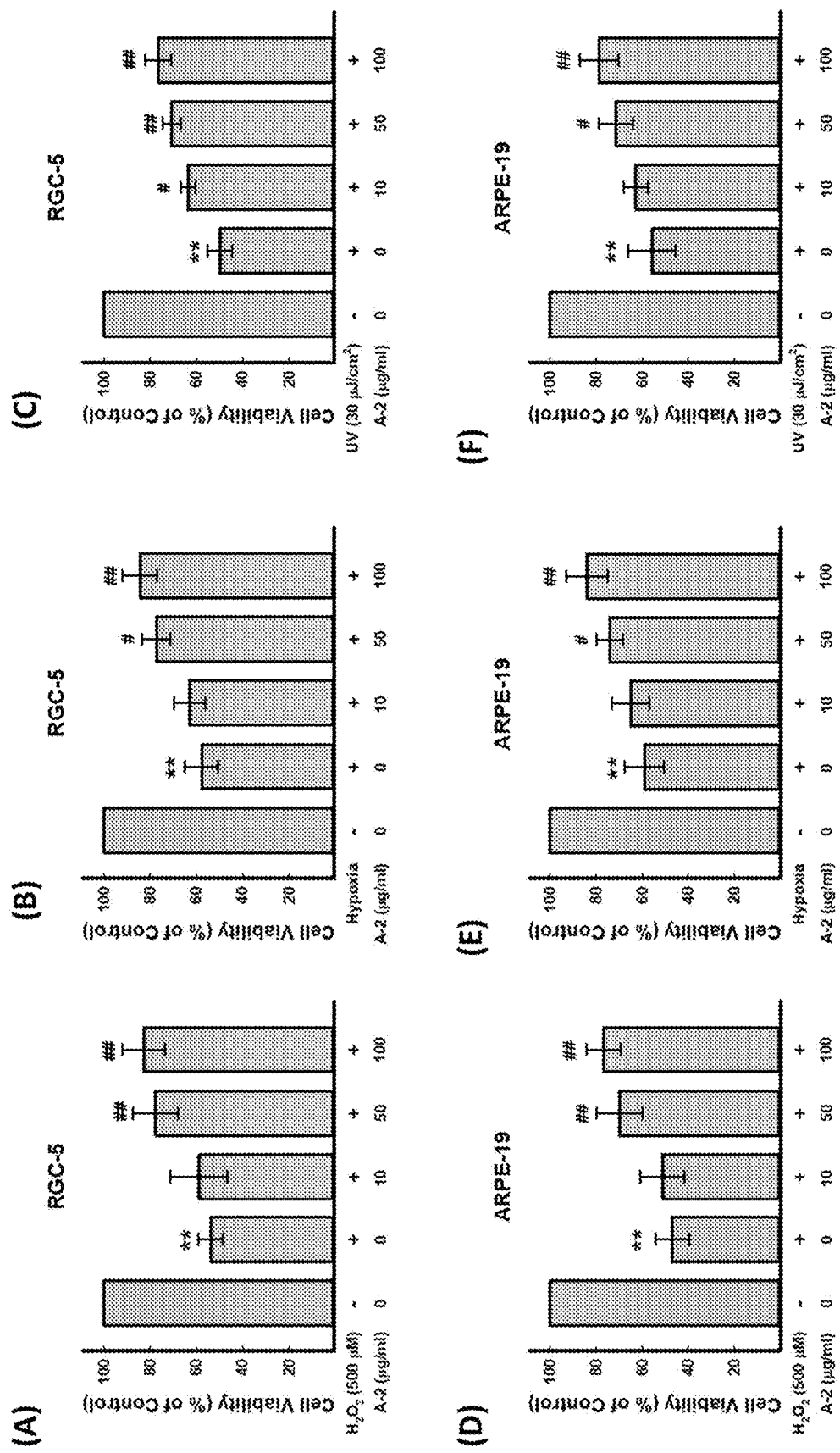
FIG. 2 shows the protection effect on RGC-5 and ARPE-19 cells with the administration of alcohol/water soluble sub-fraction A-2 from crude extract A against the damage induced by hydrogen peroxide, hypoxia and ultraviolet irradiation.

1. Extracts from Dendrobii Caulis Protected ARPE-19 and RGC-5 from Cell Injuries Induced by Hydrogen Peroxide, Hypoxia and Ultraviolet Light The macula is one of the tissues with high oxidative stress in the human body. Therefore, oxidative stress is an important cause of eye diseases and blindness. In addition, another major cause of eye lesions is omental ischemia, which is likely to cause hypoxia in cells surrounding the omentum, resulting in cell necrosis. Accordingly, we have established oxidative stress (H$_2$O$_2$), hypoxia-induced stress and UV light damage as models for screening the compounds with eye protection activity. FIG. 1 and FIG. 2 show the bar graphs of cell viability of RGC-5 and ARPE-19 cells with pre-treating the crude extract A and sub-fraction A-2, in combination of treating with hydrogen peroxide, hypoxia or ultraviolet irradiation, respectively. In FIG. 1, values represent the means±SEM for three repeats. p<0.01, the statistical significance represents the group of treating H$_2$O$_2$, hypoxia or UV and without administrating the crude extract A vs. the control group without treating H$_2$O$_2$, hypoxia or UV and without administrating the crude extract A; #p<0.05 and ##p<0.01, the statistical significance represents the group of treating H$_2$O$_2$, hypoxia or UV and with administrating the crude extract A vs. the group of treating H$_2$O$_2$, hypoxia or UV and without administrating crude extract A. In FIG. 2, values represent the means±SEM.  p<0.01, the statistical significance represents the group of treating H$_2$O$_2$, hypoxia or UV and without administrating sub-fraction A-2, vs. the control group without treating H$_2$O$_2$, hypoxia or UV and without administrating sub-fraction A-2; # p<0.05 and ##p<0.01, the statistical significance represents the group of treating H$_2$O$_2$, hypoxia and UV and with administrating the sub-fraction A-2 vs. the group of treating H$_2$O$_2$, hypoxia or UV and without administrating sub-fraction A-2. The results suggest that the crude extract A and sub-fraction A-2, regardless of the ARPC-19 and RGC-5, have protection effect under the condition of 500 μM hydrogen peroxide, hypoxia or UV irradiation. The crude extract A shows a concentration-dependent effect at three treating conditions at the concentrations of 10 to 100 μg/ml, however, the significant activity is only at 100 μg/ml. The sub-fraction A-2 not only shows a concentration-dependent manner and a significant activity at the 50 μg/ml but also provides superior protective activity than the crude extract A.

2. The Active Ingredients of Dendrobii Caulis has Cytoprotective Activity

Figure 3:
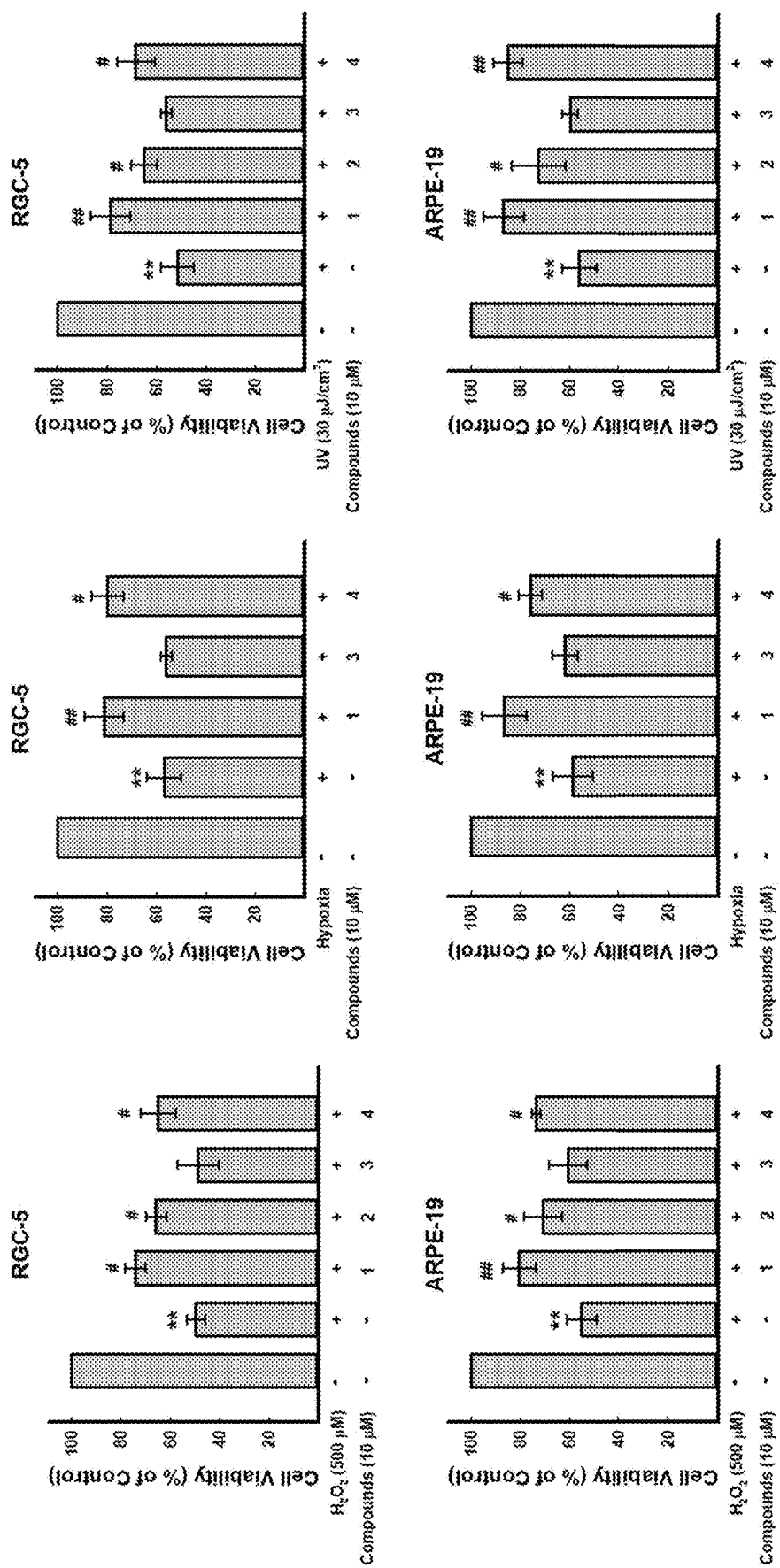
FIG. 3 shows the protection effect on RGC-5 and ARPE-19 cells with the administration of compound 1, compound 2, compound 3 and lutein against the damage induced by hydrogen peroxide, hypoxia and ultraviolet irradiation.
Figure 4:
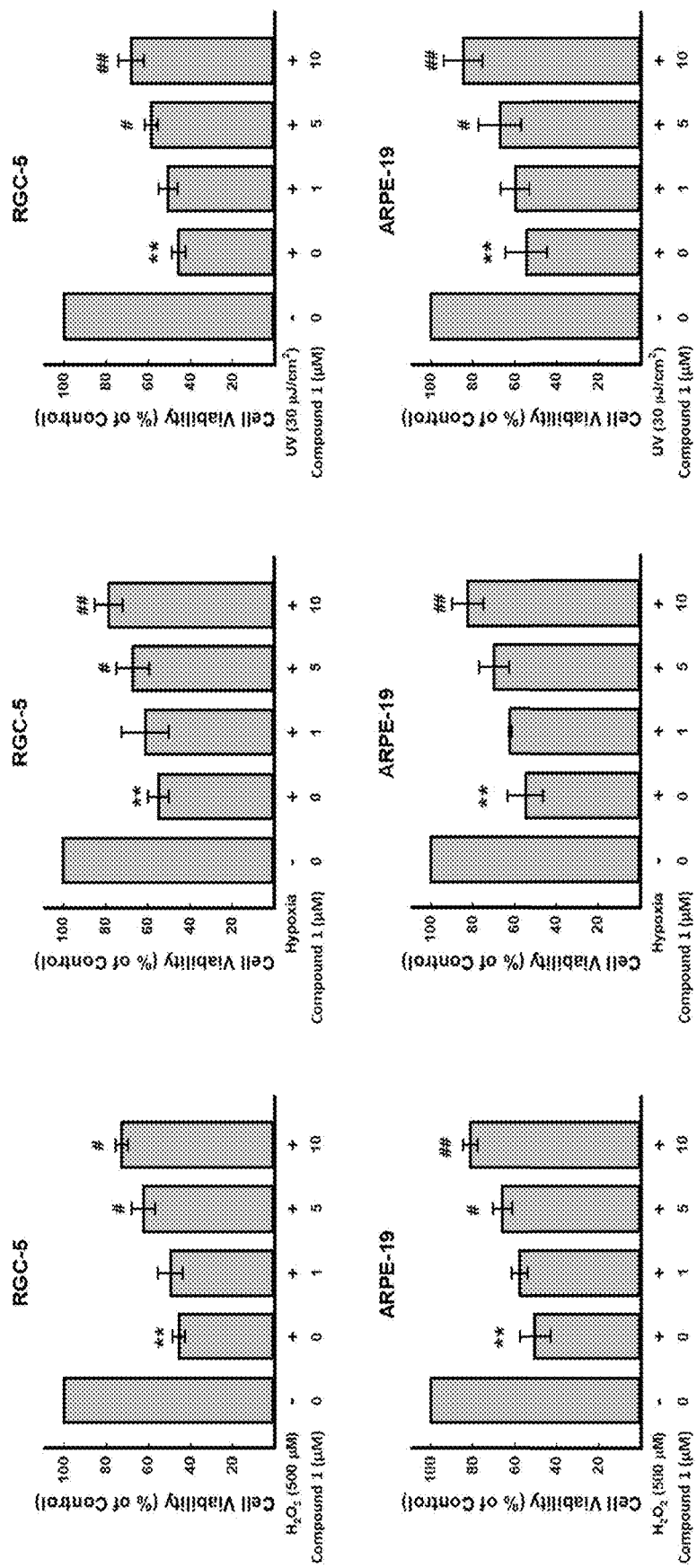
FIG. 4 shows the protection effect on RGC-5 and ARPE-19 cells with the administration of compound 1 at different concentrations against the damage induced by hydrogen peroxide, hypoxia and ultraviolet irradiation.

FIG. 3 shows the bar graphs of cell viability of RGC-5 and ARPE-19 cells with administrating with compound 1, compound 2, compound 3 and lutein (compound 4 in FIG. 3) in combination of treating with hydrogen peroxide, hypoxia and ultraviolet irradiation. In FIG. 3, values represent the means±SEM for three repeats.  p<0.01, the statistical significance difference represents the group of treating H$_2$O$_2$, hypoxia and UV and without administrating the compounds vs. the control group without treating H$_2$O$_2$, hypoxia and UV and without administrating the compounds; # p<0.05 and ## p<0.01, the statistical significance represents the group of treating H$_2$O$_2$, hypoxia and UV and with administrating the compounds vs. the control group. As shown in FIG. 3**, the main of sesquiterpene compound isolated from *D. nobile*, compound 1, can protect ARPC-19 and RGC-5 from cell being injured caused by hydrogen peroxide, hypoxia or UV irradiation, and the protective effect is superior to lutein. Another sesquiterpene compound, compound 2 can also protect against hydrogen peroxide and ultraviolet light, and its protective effect is comparable to lutein (compound 4 in FIG. 3). Conversely, the indicating component of dendrobine (compound 3) does not show enough protective activity. Please refer to FIG. 4, which shows the bar graphs of cell viability of RGC-5 and ARPE-19 cells with administrating with compound 1 at different concentrations in combination of treating with hydrogen peroxide, hypoxia and ultraviolet irradiation. In FIG. 4, values represent the means±SEM.  p<0.01, the statistical significance difference represents the group of treating H$_2$O$_2$, hypoxia or UV and without administrating compound 1 vs. the control group without treating H$_2$O$_2$, hypoxia and UV and without administrating compound 1; #p<0.05 and ##p<0.01, the statistical significance difference represents the group of treating H$_2$O$_2$, hypoxia and UV and with administrating compound 1 vs. the group of treating H$_2$O$_2$, hypoxia or UV and without administrating compound 1. As shown in FIG. 4**, compound 1 shows a concentration-dependent protective activity at a concentration of 1-10 mM under hydrogen peroxide, hypoxia or UV treatment, on both ARPE-19 and RGC-5 cells, achieving a protective activity of more than 80% at a concentration of 10 mM and showing no toxic reaction.

Figure 5:
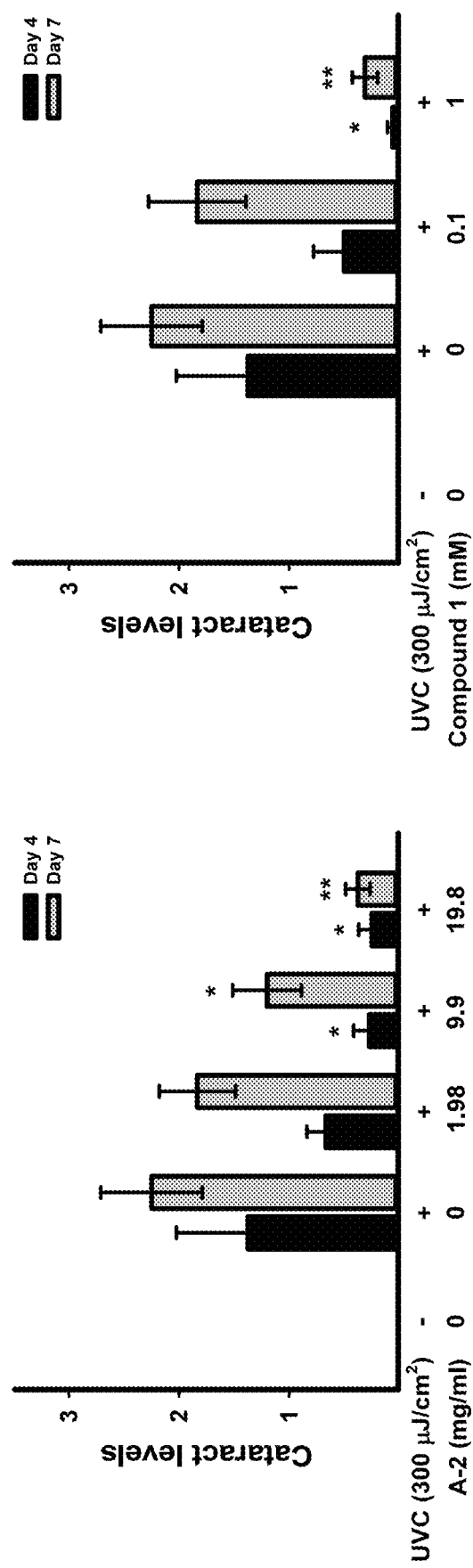
FIG. 5 shows the bar graphs indicating the severity of cataract on zebrafish induced by UV irradiation with the administration of sub-fraction A-2 and compound 1.

3. Sub-Fraction A-2 and Compound 1 from Dendrobii Caulis Protect Zebrafish from UVC-Induced Cataract FIG. 5 shows the bar graphs indicating the severity of cataract on zebrafish induced by UV irradiation with administrating with sub-fraction A-2 and compound 1. In FIG. 5, Values represent the means±SEM. *: the group of treating UV and with administrating sub-fraction A-2 or compound 1 vs. the control group of treating UV and without administrating sub-fraction A-2 or compound 1, p<0.05; : the group of treating UV and with administrating sub-fraction A-2 or compound 1 vs. the control group of treating UV and with administrating sub-fraction A-2 or compound 1, p<0.01. As shown in FIG. 5**, the UV treated group without compound 1 administration leads to catarats on the fourth day, whereas sub-fraction A-2 administration can avoid cataracts on either the fourth or the seventh day, at the concentrations of 0.495-4.95 mg/ml, and compound 1 can significantly reduce the occurrence of zebrafish cataract at 0.1 and 1.0 mM, especially at 1 mM concentration, in which almost no cataract occurred on the fourth day.

Those skilled in the art will readily observe that numerous modifications and alterations of the device and method may be made while retaining the teachings of the invention. Accordingly, the above disclosure should be construed as limited only by the metes and bounds of the appended claims.

What is claimed is:

1. A pharmaceutical composition with eye care effect, comprising a pharmaceutically acceptable carrier and an active ingredient, wherein the active ingredient comprises a therapeutically effective amount of 2β, 3β, 11, 12-tetrahydroxypicrotoxan-3(15)-olide 11-O-β-D-glucopyranoside.

2. The pharmaceutical composition with eye care effect according to claim 1, wherein the active ingredient is extracted from the stem of Dendrobii nobile.

3. The pharmaceutical composition with eye care effect according to claim 1, wherein the active ingredient has a weight percentage of 12-20%.

* * * * *